(12) United States Patent
Simmons

(10) Patent No.: US 7,463,929 B2
(45) Date of Patent: Dec. 9, 2008

(54) INTELLIGENT ASSISTED CONTROL OF LIVING BODIES

(76) Inventor: John C. Simmons, 7993 Cavershamwood La., Germantown, TN (US) 38138

( * ) Notice: Subject to any disclaimer, the term of this patent is extended or adjusted under 35 U.S.C. 154(b) by 663 days.

(21) Appl. No.: 10/718,348

(22) Filed: Nov. 21, 2003

(65) Prior Publication Data
US 2005/0119702 A1 Jun. 2, 2005

(51) Int. Cl.
*A61N 1/05* (2006.01)
(52) U.S. Cl. .............................. 607/58; 607/2; 601/46; 54/71; 340/573.1
(58) Field of Classification Search .............. 607/2, 607/58; 601/46; 340/573.1; 54/71
See application file for complete search history.

(56) References Cited
U.S. PATENT DOCUMENTS

| | | | |
|---|---|---|---|
| 4,335,682 A | 6/1982 | Gonda | |
| 4,764,111 A * | 8/1988 | Knierim | ......................... 433/5 |
| 4,898,120 A | 2/1990 | Brose | |
| 4,919,082 A | 4/1990 | Tsai | |
| 5,046,453 A | 9/1991 | Visci | |
| 5,351,653 A | 10/1994 | Marishen | |
| 5,566,645 A | 10/1996 | Cole | |
| 5,749,324 A | 5/1998 | Moore | |
| 5,809,939 A | 9/1998 | Robart et al. | |
| 5,815,077 A | 9/1998 | Christiansen | |
| 5,857,433 A | 1/1999 | Files | |
| 5,868,103 A | 2/1999 | Boyd | |
| 6,047,664 A | 4/2000 | Lyerly | |
| 6,232,880 B1 | 5/2001 | Anderson et al. | |
| 6,273,027 B1 | 8/2001 | Watson | |
| 6,334,073 B1 * | 12/2001 | Levine | ......................... 607/58 |
| 6,352,053 B1 | 3/2002 | Records et al. | |
| 6,430,450 B1 | 8/2002 | Bach-y-rita | |
| 6,571,193 B1 | 5/2003 | Unuma | |
| 6,591,786 B1 | 7/2003 | Davis | |

* cited by examiner

*Primary Examiner*—Carl H Layno
*Assistant Examiner*—Deborah Malamud

(57) ABSTRACT

An apparatus and process for providing assisted control, direction, and other information to a living being through a stimulation-based interface.

30 Claims, 3 Drawing Sheets

INTELLIGENT ASSISTED CONTROL OF LIVING BODIES

BACKGROUND OF THE INVENTION

There have always been situations where animals and even people have needed direction and information about a desired direction for them to take. Then, as now, it is typically associated with pain. There have been and are a plethora of aversive behavior devices presumably beginning with the stick, then the whip and, more recently by electronics-based aversive stimuli.

In U.S. Pat. No. 6,571,193 Unuma, et al., awarded May 27, 2003, provides a recognition system of actions done by the body wearing special equipment, ex: the reporting by radio of the motions or actions of a body to which sensors, such as GPS or motion sensors, are attached to a remote place where they can be analyzed. This allows, for example, an animal to be tagged with a sensor and the owner to know where the animal is (GPS) and what he is doing (walking, running, etc.)

Anderson, et al., in U.S. Pat. No. 6,232,880, teach, for applications such as keeping cattle in a desired pasture area, the aversive, punishment-based prodding of an animal in a binary direction (left or right) sensitive to the animal's position reported by GPS sensing for keeping the animal in a contained area such as a square. The prodding is aversive only and prods to the left or right with any gradient used dedicated to the amount of punishment to be applied based on how close the animal is to some or any forbidden boundary. The device uses GPS not to report its position to a remote intelligence but to decide when to prod and/or punish the animal left or right away from any fence which is based not on a desired direction but on preventing the crossing of an imaginary boundary with physical discomfort resulting in usable fear.

In U.S. Pat. No. 5,815,077, Christiansen provides aversive "barking-collar" and other bad-behavior punishment as well as an audible sound from the animal-attached assembly for easier location by a farmer, etc. In U.S. Pat. No. 6,047,664 Lyerly teaches a shock-leash for the aversive only training of things not to do. Also, in U.S. Pat. No. 5,868,103 Boyd describes a device emitting a painful or noxious fluid or substance to produce an "adverse effect". In U.S. Pat. No. 5,857,433 Files describes an aversive stimulus device on an animal combined with a GPS reporting device controlled by a hand-held device that also reports to the holder the location of the animal. In U.S. Pat. No. 6,273,027 Watson, et al discloses an automated system analogous to a candy dispenser to reward good actions. Also, U.S. Pat. No. 4,335,682 issued to Gonda et al. on Jun. 22, 1982 describes a remote control animal collar that emits electrical shocks followed by sounds. U.S. Pat. No. 5,749,324 issued to Moore on May 12, 1998 describes a high-frequency sound burst creating collar responsive to barking of a dog and also can be activated with a remote control. U.S. Pat. No. 5,351,653 issued to Marishen et al. on Oct. 4, 1994 is has a hand-held electronic device providing positive audio tones in conjunction with negative ones, to, with no specifics of a desired animal response to be achieved, generally encourage good behaviors while discouraging bad behaviors. U.S. Pat. No. 5,809,939 issued to Robart et al. on Sep. 22, 1998 and U.S. Pat. No. 5,566,645 issued to Cole on Oct. 22, 1996 is based on bridle bits which that dispense tasty or pleasant fluids in the horse's mouth. It has been observed, however, that the combination of punishment and positive reinforcement confuses the animal.

In U.S. Pat. No. 6,352,053 Records, et al. teach of providing an electric shock under a horse's saddle to make the animal buck, etc. Davis, in U.S. Pat. No. 6,591,786 teaches a device for guiding animals by placing an earphone in their ear so they can hear their master's verbal instructions. Moore in U.S. Pat. No. 5,749,324 adds to the shock collar the interpretation of the human voice or other sounds to the animal to decide when to apply aversive shocks or other stimulations. Vinci, in U.S. Pat. No. 5,046,453 further encourages the animal to positive behavior by emitting a cold fluid on its skin. Brose, in U.S. Pat. No. 4,898,120, as some of the others above, adds noxious sounds, etc. to discourage the breach of a zone.

Perhaps Tsai, in U.S. Pat. No. 4,919,082, best embodies the existing paradigm favoring aversive behavior control with an electric collar that tightens around the animal's neck for a graduated choke effect (not unlike the familiar screw-based hose clamp) to encourage it from bad behavior and potentially put it out of its misery.

Bach-y-rita, et al, in U.S. Pat. No. 6,430,450 established the effectiveness of communicating signals to the human tongue and the brain's effectiveness in learning to perceive those stimulations to the tongue as spatial information intuitively processable through brain plasticity. They also developed equipment that effectively delivers stimulations painlessly.

SUMMARY OF THE INVENTION

It is an object of the current invention to provide a non-punishment-based means of directing a body.

It is also an object of the current invention to provide a positive and precise directional control capable of, rather than being analogous to a push from one side, providing a immediately recognized, spatially intuitive, and precise desired direction with that instant perception eliminating any need for a long, slow and tedious series of pushes or prods executed against the body until the final accomplishment of what is, in the end, only one desired instruction.

It is also an object of the current invention to provide such a precise and intuitive directional communicating device that it can also be useful in providing direction to humans where auditory communication is difficult.

It is also an object of the current invention to provide negative reinforcement only as an exception for those rare occasions when the clear, spatially precise directions are ignored, thus allowing the body to be directed for long duty cycles without any of the depression or body-wearying effects of continual pain and discomfort.

It is also an object of the current invention to provide a fully automated training method for teaching behavior as managed by a computer program rather than draining training resources.

It is also an object of the current invention to make it possible to direct animals to perform extensive and precise operations.

It is also an object of the current invention to make it possible for birds to be usefully directed despite anatomical problems.

DESCRIPTION OF THE PREFERRED EMBODIMENTS

Figure 1A:
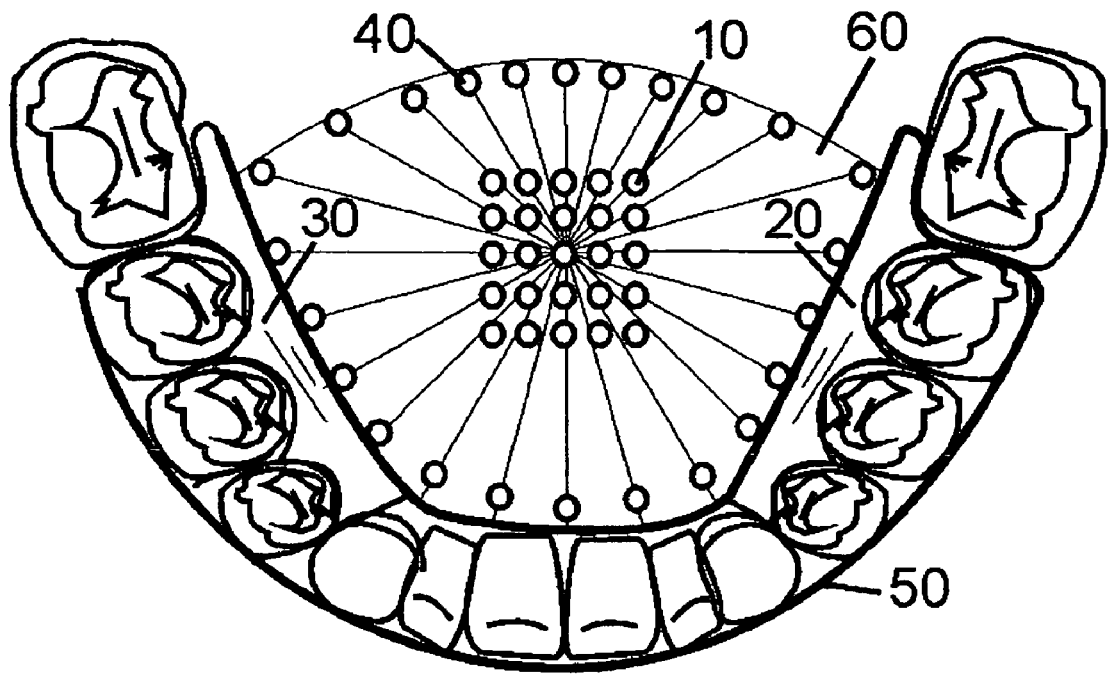
FIGS. 1A and B illustrate one embodiment of the director configured here for a human. A matrix of stimulators also referred herein as nodes, 10 and 40, are shown in the central area of the director arrayed on a substrate, 60, which director is shown here in a form for mounting in the upper mouth like an orthodontist's retainer. Another array of nodes, 40, surrounds the area representing here one every 15 degrees of rotation (as shown in FIG. 1B with the radiating rays) from the approximate center of the director. A wire, 50, anchors the director to the teeth and serves as an antenna for transmission from the behavior controller, 20. 30 is a battery for power.

As shown in FIG. 1, as applied to a human mouth, the director can fit in the mouth anchored by wire and/or molded fittings and be removed and replaced as easily as an orthodontist's retainer or be more permanently anchored. As shown in FIG. 2, the director's stimulator array(s), called nodes, as well as other director elements, may also be placed on other areas of the body. For convenience here, the director will be referenced for the most part without concern for its location. However, where the application permits it, the orally located director of FIG. 1 is by far the preferable embodiment because:

a) the tongue has no dead skin (it is the only surface area of the body where stimulations don't have to be excessive to overpower a layer of dead skin that, unfortunately, varies over time causing stimulations to be too strong or too weak) and b) the tongue also has an extremely dense nerve map that is provided by the brain and c) the brain has, for the tongue, an already ideal spatial position cognizance (we have a clear spatial image of where a stimulation on the tongue occurs) on that very high resolution nerve map and d) the tongue is the ideal location for pleasurable and/or distinctly perceived stimulations because of the exceptional sensitivity of that area.

To direct the body, a signal is transmitted to the communicator 20 causing the desired nodes to act. A behavior controller, normally located in the communicator housing 20, determines what each node is to do. This behavior controller can range from a relatively dumb switching device to send a received-via-transmission signal to wires leading to particular nodes, to a tiny ASIC, to a full blown processor; depending on the application and the director's available real estate which are often pre-determined by the size of the wearer.

The stimulations can be pleasant to interruptive vibrations where the nodes are miniature voice coils or other forms of vibrator or transducer. They can also be temperature-based where the nodes change the temperature either cooler, where the arrays 10 and 40 are Peltier plates connected to a DC voltage from the power supply 30 or an external power supply, or hotter, where the arrays are resistance based, Peltier, or other heating means. Stimulations can also be low level electric stimulations well below any pain threshold. The tongue has no dead skin and prior research has established effective signal recognition in the very low millivolt and milliamp range. Where necessary, a higher voltage may be also used to correct behavior. Pleasant stimulations including those of electrically induced taste may also be used. Useful combinations of the above forms of stimulation will be obvious particularly in the practical areas of training animals where behaviors can be directed by a pleasant cool point on a hot tongue or, as a strong contrast related to training differentiation of a direction to follow as opposed to a painful threat to be avoided, a stiffer electrical charge to indicate a danger or direction to be avoided.

Stimulations can be point-based, pattern based, or action based. If, with the embodiment of FIG. 1, you want to direct the body to move in a direction that is 45 degrees to the right of the current body direction, there are several effective means that can be used individually or in combination.

a) Point-based: The simplest and least interruptive and often easiest to perceive is to use the point-based directional cues of the director's external ring 40. Since, in the illustrated embodiment of FIG. 1, the ring's nodes radiate in 15 degree increments from center, to indicate that 45 degree desired change in body vector, requires only the stimulation of the third node right of the top center node (which is 45 degrees from center) which "points" the user precisely in the desired direction. Of course more nodes permit even more precision. However, at least for electronic stimulation, research has shown that, for example, to indicate a desired direction of 52.5 degrees (midway between the 45 degree node and the next one to the right, i.e. the 60 degree node), you need only stimulate the nodes on both sides and the brain's perception averages the two to a singular location. This makes it possible to double the resolution of the matrix.

b) Pattern based: That same 45 degrees of desired change can be communicated to the director's wearer by stimulating the members of the node array 10 that occur on the 45 degree diagonal line of that array.

Early research on the underlying elements of this design were performed with a 12×12 matrix with excellent results. Matrices with thousands of points of resolution are now being produced making this option substantially more desirable and extremely well perceived. Somehow we perceive direction better from a long arrow than just a point on the horizon. A combination of A and B provide an even more accurately perceived direction.

c) Action based: A more interruptive but even more accurately perceived and insistent directional option is the action based option. Here, like in pattern based, a line is drawn and optionally "capped" with the appropriate node on the ring 40. However, here the line is drawn sequentially starting, in this 45 degree moving forward example, at the bottom left of the matrix 10 all the way up to the top right and then extending to the third node to the right of center on the ring 40.

Other recognizable signal strategies and graphical designs will be obvious including creating arrows that point forward and/or left/right to incline the head down and to the left or right (thus intuitively "pulling" the head in that direction which causes it to go down) and arrows towards the back of the mouth and/or left/right to appear to "push" the head backwards and/or left or right.

The behavior controller 20 may include any combination of data transmission facility, computer processors, sensors, memory, and/or signal modification or transduction for the particular stimulators used. Some embodiments, may involve no communications outside the director but may be limited to sending direction commands from the processor to the stimulators. This can be a stand-alone direction requiring no remote control and can include as sensors GPS, etc. to autonomously direct a path or a zone to cover.

The controller 20 is appropriately be called a "behavior controller". It may also include as all or part of the current invention's data transmission facility, which may be limited to a receiver for many applications that require only a one-way communications such as from a remote person giving directions. In other applications, some of which are mentioned below, embodiments with a transmitter are used to, for example, provide feedback to a remote person who is monitoring and/or giving directions. The transmission and reception may be accomplished by radio, hard wire, infra-red or any useful means of transmitting data from the oral device to nearby body worn equipment where it may be used or relayed by additional an additional body worn communicator to a remote computer or operator or, where the controller's on-board transmission range is adequate for the distance, directly to a remote computer and/or operator. In an embodiment that conserves or limits by design the power of the controller, the controller itself is a very short-range radio transmitter and receiver which reaches a nearby transmitter and receiver with more power and/or range and is, ideally, worn just inches away on the body.

That nearby transmitter and receiver and any desired additional body worn equipment may be placed in a storage compartment which can contain anything that won't fit in the oral device itself and can be located anywhere on the body or close by. These additional devices can be easily connected to the director via the communicator. For example, additional processors can be placed in the storage compartment for making use of that relayed data from the director.

A few examples of additional devices:

Relay devices: Where the communicator's range or capacity is inadequate, a storage compartment stowed transmitter can extend the effective range.

GPS reception, either located in the director itself or stowed in the storage compartment, allows the processor in the director or in the storage compartment to direct the body to stay within a defined geographic area or follow a specific path based on a map or other instructions such as vector lists and latitude/longitude "fences".

GPS directed from a remote computer or operator is accomplished by the transmission of the GPS position to that remote entity and the reception of specific desired responses back resulting in the logical directional stimulations.

Compass direction, which can come from a stowed compass or simple integration of GPS positions over time, also facilitate the remote operator or computer's direction of the wearer.

A video image of the wearer's environment from a body worn camera whose image is transmitted to a remote operator allows the remote operator to guide the wearer visually with great precision.

These last 3 abilities together are particularly effective in enabling a remote operator and/or computer to silently but precisely direct the director's wearer with great precision and responsiveness to the wearer's visible and geographic environment.

There are also numerous user interfaces available for a remote handler to use to guide the wearer of the director. There are many different methods for their use to calculate and execute stimulations to accomplish this task that are within the current invention. One sample configuration is illustrated below for continuity between the examples below of peripheral device examples.

Steering wheel: The steering wheel, based on the well-established gaming interfaces, converts the position of the steering wheel to lateral directional stimulations on the director. Although any of the nodes in FIG. 1A or FIG. 1B or any other configuration of nodes could be used, we will discuss only the ring 40 for lateral turns in these examples. So, as the handler turns the wheel to a relative yaw (compared to the current direction vector) of 15 degrees, the computer interface, as in gaming applications, sends an output signal to the director. In this embodiment, that output signal is converted to a choice of stimulation point(s) and, in this example, that is (since the yaw change is positive) the node just right of top center since that represents the ray (see FIG. 1B for rays) that is 15 degrees positive.

In the course of the turn, it will be normative for the node location-based stimulations to be progressive. When, for example, the wearer is stimulated to turn 30 degrees to the left, initially the second node left of top center on the rim 40 is stimulated indicating 30 degrees (twice the 15 degrees per node used in this simplified example). However, the stimulation locations can change with relation to the remaining degree of turn desired. In the example, after the wearer accomplishes 15 degrees of the desired 30 degree turn, the system or the user using a steering wheel, will naturally back off just as in any turn, to a now-desired turn stimulation of only 15 remaining degrees (i.e. the first node left from center) and continue to decrease until no directional stimulation at all is created or an "on target" stimulation, normally at top center, is given to indicate perfect direction.

Thus, the handler can "drive" the wearer much like, and as simply as, a car.

Elevators: Since not all wearer direction is on the ground, a means of controlling pitch is also useful. One peripheral device for controlling pitch is a foot or otherwise controlled elevator which simply demands a given amount of increased or decreased pitch. In these examples, the grid, 10, is used for communicating pitch required (although other nodes could be used and these same nodes could also be used for other purposes). For downward pitch, where the head will rotate forward the array points forward and, for upward (positive) pitch where the head must rotate backwards, the array points backward. This intuitive "push the head the way you want it to go" is just one of multiple but intuitively sensed means for communicating pitch commands.

Joystick: The joystick can, as in gaming applications, be configured to replace both the steering wheel and the elevators.

It should be noted that, though these above examples of using specific pointing devices to control the head's pitch and yaw do so by indicating pitch and yaw separately on different nodes, it is also intended that many embodiments will use the obvious geometry of the matrices to point by singular direct net angles for more intuitive and rapid response. An example of the latter method follows in the mouse example.

Mouse or other pointing technologies: The handler will often be viewing the progress and position of the wearer on a head-worn camera whose image is transmitted to the handler who may be viewing it on a screen or head-worn display. The handler may then choose a point of reference on the screen with a mouse cursor or other pointing or selection device. As an example, assume the handler clicks a point on the screen that is displaying the wearer's view towards the top right of the screen defining a point resulting in a directional change of 45 degrees (a vertical line running from the center of the screen straight up to the top would have to rotate 45 degrees around the center point for the line to intersect the chosen point). At the same time, the distance from the center of the screen to the point selected demands that we move a distance (in the direction just chosen) applicable to a rotation along the Saggital plane of, for example, 15 degrees. The handler has demanded that the wearer raise the head upward and to the right and this method commands both at once. The handler has thus defined both the direction and distance of change, both of which may be thought of in degrees of rotation along an axis (the direction in degrees of rotation on the wearer's and camera's coronal plane and the distance, how far in that direction, in degrees rotation along the Saggital plane that crosses both the center of the user's field of view and the point to be accomplished).

Direction: In this example the direction is 45 degrees (to the upper right). How does the computer calculate that?

Direction calculations: The degrees of rotation of an imaginary line that extends from the middle of the screen to the top middle (straight up) to any point clicked by the handler is easily calculated and, when calculated, is directly analogous to the congruent desired change along the plane of the view of the camera and wearer (the coronal plane). In pixel math, the angle of directional change is calculated as:

$$\theta = \arctan(Px/Py)$$

where θ represents the degrees of angle adjustment along that coronal plane, Px is the number of lateral pixels between center of the screen and the point chosen, and Py is the number of vertical pixels between the center of the screen and the point chosen.

Distance: The distance is then calculated against the position of the center of the screen (i.e. the camera's center of field of view) or other positional calculation for the amount of adjustment needed. This number of pixels (or other measurement) difference is converted to at least the approximate number of degrees of change (distance) required for the wearer's head to point where the handler wants. For head pointing applications we can optionally identify the plane of the matrices shown in FIG. 1A and FIG. 1B with the head's coronal plane so that, in terms of distance, a point higher on the matrix 10 might mean a higher distance/angle i.e. more change/distance desired. The director thus guides the wearer with stimulations.

How the computer calculates Distance:

A given number of pixels on the screen (if the handler has zoomed beyond the view seen by the wearer the calculation is then based on the un-zoomed pixel map) can table select to a good approximation of the number of degrees of behavior change desired for outdoor working distances. However, the precise, un-approximated number of degrees of change to a handler-selected position is related to the distance which may be more accurately measured or approximated by the camera's focusing mechanism (up to about 28 feet being considered infinity) or a body or camera-mounted distance sensor which is then installed and used according to the equation:

$$\alpha = \arctan(H/D)$$

where α is the angle of change required along the head's Saggital plane (how far the head is to move in the direction already calculated), D is the sensor-returned distance which serves as the hypotenuse, and H is the height (distance between the selected point of reference and the current center of view) in terms relative to those of D such as meters which is itself taken from the number of pixels between the desired point and the handler-indicated point times a conversion factor from a table of pixel relative sizes by distance applicable to the optics being used or other effective calculation.

Thus the director can control direction in multiple planes simultaneously for complete 3-D body control. This example uses the combined directions method rather than using one set of sensors for pitch and another set for yaw. Thus, in this mouse wielding handler's example, the stimulations can be any combination of these below:

a) Ring Node Method: The node whose location is analogous to the number of degrees of desired directional change (in this example those configuring the director have selected 15 degrees between the ring nodes) so the third node right of the top center node on the ring array 40 indicates 45 degrees and would be stimulated in a amount relative to the amount of change desired along that vector and/or b) Matrix Point Node Method: The node whose relationship to the center of the array 10 is analogous to both the degrees and amount/distance of change required is stimulated. In this example, for 45 degrees (up and to the right) all the nodes from the center point of 10 along a 45 degree line to the top right of the matrix are candidates for direction since they all trace the desired vector. However, since about 15 degrees worth of travel are desired along that line, only the node on that line next to the center point (one 15 degree increment away) qualifies for both angle and distance and thus this one is stimulated.

c) Matrix Line Method: all the nodes between and/or including the node selected in (b) and the center node are stimulated providing a clearer image (an arrow rather than just a point) of, simultaneously in a single display, both how much change is required and in what direction for easy and intuitive wearer response.

d) Moving Arrow: the nodes of (c) are stimulated in sequence starting with the center point in 10 to paint an action arrow.

Multiple nodes can, of course, be used to create thicker, more noticeable arrows. Higher node densities also permit finer gradients where needed and previous research indicates that thousands of nodes are discretely recognizable on a single director.

As mentioned above, these methods just above, can show a net direction and amount to move the head in single, intuitively obvious direction for fast learning rather than defining separately the pitch and yaw separately on different nodes. However, there are applications where separate pitch and yaw instructions will be desired and, in some cases, they will be even be executed sequentially (ex: stimulating a ring node first to attain the desired yaw and then stimulating the matrix, 10, to attain the desired pitch rather than just pointing "go 45 degrees for this far" all at once). In these applications, A-D above can be modified with one acceptable modification being the matrix points, lines, or arrows in B-D can point a yaw of 0 or 180 degrees (tilt the head forward or backwards) with line lengths and/or node amplitudes or signals indicating the distance to accomplish in that dimension.

Thus the same equipment can perform multiple methods of directions applicable to the job at hand.

Bachy-y-rita's previous research associated with the patent listed above established the rapidity with which the brain can learn to recognize and respond to patterns of electric stimulations on the tongue. The current invention, whether placed on the tongue or other sensitive parts of the body and whether using electric stimulations, pleasant Peltier cooling on points, interruptive vibration (for contrast with the more pleasant alternative), or other stimulations or combinations of these can be used to provide precisely graduated travel directions in real time right down to the number of degrees of turn, as illustrated above, as well as level of importance, which is provided by the amplitude of the stimulation and/or the beats of the stimulation (i.e. the periodic repeating pattern and/or frequency or other recognizable pattern of stimulations chosen).

Thus, the current invention can be used to speed animal training where not only is bad behavior punished and a binary left or right turn suggested but:

1. Bad behavior can be indicated, at any level of purely "academic" (i.e. painless) communication as a learned position on the matrix.

These stimulation(s) (as described in A-D above) can also carry with it a specific directional instruction to solve the bad behavior such as go 10 degrees left. How far or fast to go can be communicated with amplitude or stimulation pattern or frequency.

2. Bad behavior can be indicated, at any level of purely "academic" communication as a direction sensitive pattern.

3. Bad behavior can be indicated, at any level of purely "academic" communication as a moving arrow across the entire tongue to "paint" the precise direction of the desired correction. For example, if the bad behavior is an off course yaw of 10 degrees, the correction may be an academic 10 degree moving arrow (or one of the other stimulation pattern options) in the more desirable direction. A very strong stop signal that is interruptive but still can be academic is a moving arrow painted to the rear of current yaw (180 degrees from current course).

4. A desired good behavior can be painlessly directed using any combination of 1-3.

5. A desired good behavior can be painlessly emphasized by degrees or patterns of stimulation indicating not only where to go or what to do (stop, turn around, point the head this way, etc.) but also how fast, with what immediacy or importance.

6. A non-action (stop cold) command is easily communicated and learned using any of the above techniques. One pattern is to pulse stimulate once (or intermittently until the response is accomplished) the entire matrix 10 for "freeze".

7. A pleasure response (whether a Peltier cool spot or array of spots on the hot tongue of, for example, a hot dog in heavy training exercises, or whether an electrically stimulated taste associated with reward, a stimulating vibration associated with rewards during training, or a cessation of an irritating stimulation i.e. it feels good when that stops, etc.) delivered remotely through the director speeds learning with positive reinforcement to augment or replace negative reinforcement.

8. An affirmative, encouraging response, as shown by Pavlov and his canine assistant, can be very rapidly learned by association. Any stimulation pattern, whether it be a rapid sequential circling of stimulations around the node ring and/or a pleasurable vibration on the back of the tongue, a Peltier cooling point, or any other recognizable signal, can be, especially when associated with a reward, even a delayed reward, during training, be very rapidly associated with "good job".

9. Similarly, a negative pattern can also be recognized which may be, during training, accompanied by a mildly painful stimulation, which, after training is no longer needed because the pattern itself says "no".

10. Positive, pleasurable stimulations may also be effected by the placement of nodes in or on erogenous zones for communicating a positive response to a behavior. One example is a vibration based node. In some species such as raptors such as falcons the females are more effective at endurance and obedience and are easily set up with such equipment whose position in the vaginal area is more easily maintained by a non-obstructive retaining line attached to the tail-loop assembly (with that assembly being described in further detail below). The effectiveness and behavior modifying nature of such stimulation in animals is well documented including the willingness of salmon to overcome any obstacles to reach spawning grounds. As a positive, if infrequent and very brief, reward for good animal behavior, it is useful for positive training reinforcement in lieu of negative only.

11. The amplitude and/or pattern of the stimulation can be increased all the way up to a painful signal that, while less academic, not only encourages obedience but removes all doubt what obedience involves with a clearly defined direction and speed of response desired.

12. The matrices are also ideal for creating recognizable patterns that can identify a command such as take off, land, freeze, return, etc.

Even without external communications being used, the stimulation controller in the director can have sufficient memory to direct a complex and continuing series of commands and even responses to failures to respond immediately to commands such that a complex series of actions can be replicated. It may be a trivial application of the current invention but, for example, the entire act of a circus animal could be reduced to a time-spaced series of director commands (with optional corrections where not followed as sensed by worn sensors) helping the wearer to recall what comes next, staying in time (particularly where multiple wearers need to be synchronized), and staying in the planned "groove" of each step of the potentially very complex learned behavior.

Not only does the current invention provide a rapid means of precision training, it provides a rapidly learned protocol for precision direction from a potentially remote handler. For example, using conventional techniques it is impossible to direct an animal to follow a precise path much less to be able to direct that animal to "point" and maintain the point to a previously unselected handler-desired object (they can learn to point to a duck but not to the specific one the handler selects from an area of particular handler interest and even then not a true azimuth and elevation point but just a proximal rotation of the Saggital plane). Using the current invention, the animal can be rapidly trained to follow precise directional commands in real time from the handler while, for example, the handler is viewing the animal's view from a transmitted head mounted camera view. Additionally, using the current invention, the animal can also then be precisely directed to point the head mounted camera or other equipment to a precise point indicated by the handler with a mouse cursor-on-screen image or other pointing device.

With the addition of actuators or radio controllable devices, the handler can also operate other equipment carried by the wearer.

Training animals is tedious and expensive. However, the current invention is ideally suited to automated training. By placing the wearer with a computer to run it through its paces automatically, the computer can systematically teach more and more difficult learned behaviors and obedience through rewards and penalties directed by the computer program responsive to how well the wearer followed instructions. The computer can also extensively and without bias grade the performance of the wearer by keeping statistics of successful and unsuccessful responses to instructions.

For example, placement of attitude and direction sensors in the storage compartment or in the director itself, permits the computer to request a turn 10 degrees to the left through a node stimulation which is optionally encouraged with a decreasingly noticeable (as training progresses) visual stimulation (such as a quick flash of something desirable to the wearer) at that 10 degree position relative to the position of the wearer on a computer monitor or, for larger wearers, a video projector on a screen. Successful obedience and accurate response, as measured by the sensors compared to the stimulation commands, can be rewarded by pleasant or less-unpleasant stimulation and/or any of the common goodie-dropping dispensers that are responsive to computer control.

More and more complex tasks can be completed even including immersive simulations where the wearer is following complex, computer provided commands to navigate an obstacle course, retrieve a payload, etc. responsive to node stimulations.

Similarly, the current invention is ideal for other computer directed activity including immersive-simulator-supported handler direction, autonomous wearer direction where the onboard or remote computer directs the wearer on a route, through a task, or to cover an area.

Figure 1B:
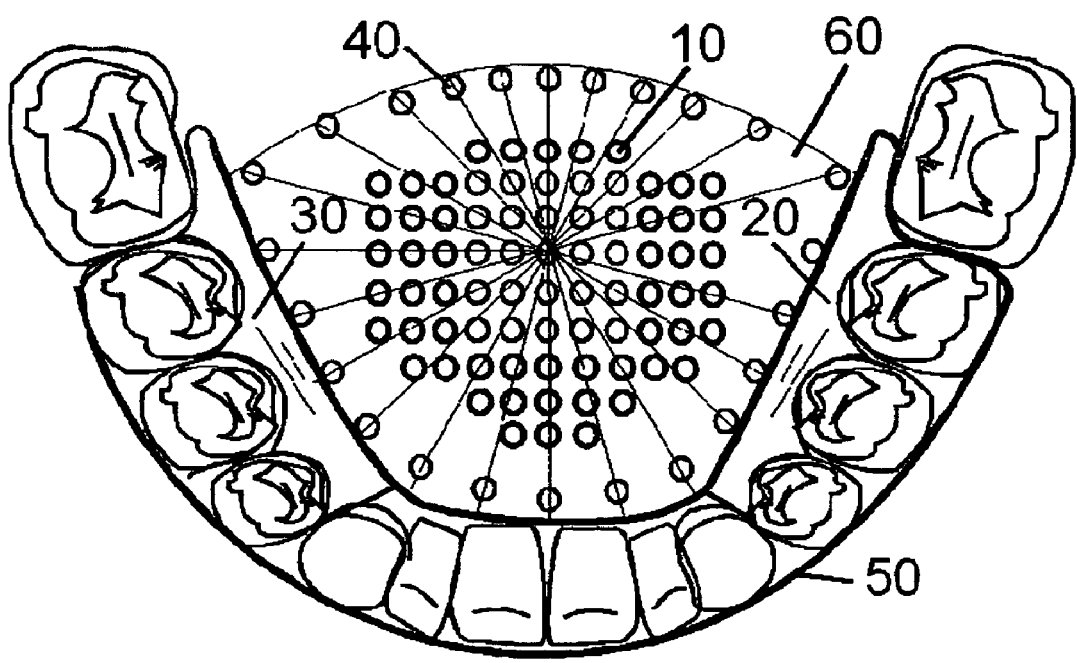
FIG. 1B also displays an array of sensors with more sensors than shown on FIG. 1A.
Figure 2:
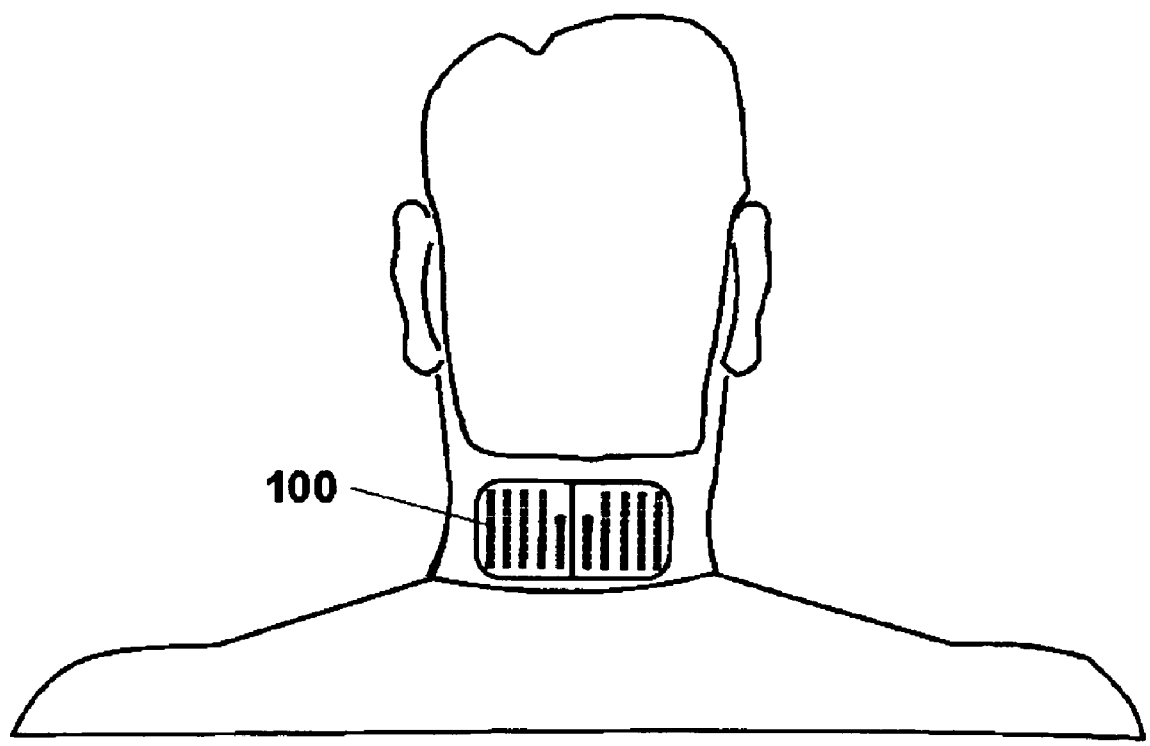
FIG. 2 is an array of stimulators, referred to as nodes, shown applied to the back of a human neck.
Figure 3:
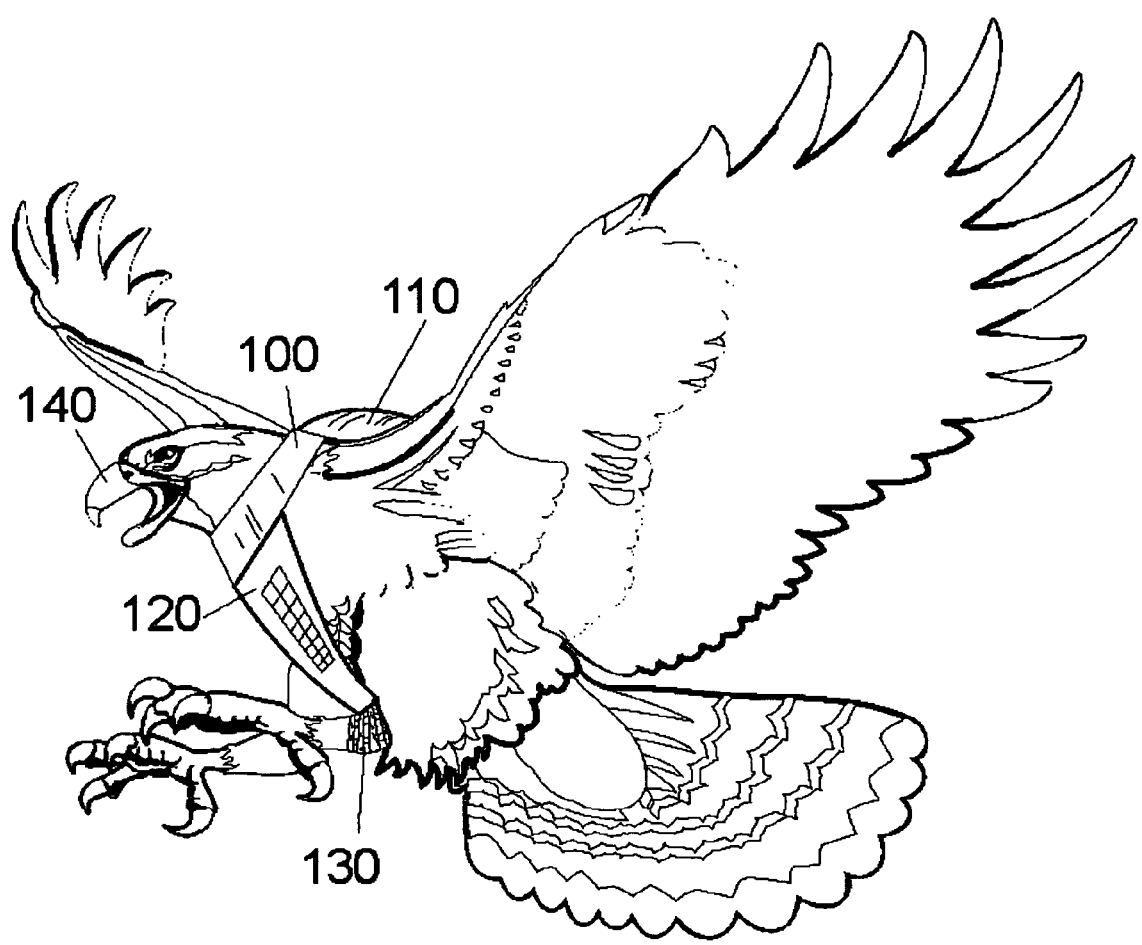
FIG. 3 shows a falcon wearing a yoke, 100, connected to a vented body garment with selected dimensions of flexibility through fiber selection, 120, carrying a payload of electronics in the storage compartment below the payload cover, 110, and stabilized from lateral shifting by leggings, 130. The leggings are connected behind to a loop around the tail (not visible) which limits forward movement of legs through leggings, 130, to protect the head assembly, and that tail loop assembly itself closes the garment by also connecting to the back strip that leads to and supports the payload cover, 110, while preventing excessive anterior and posterior shifting. An outer beak formed cover, 140, for attaching and connecting the inside-the-beak assembly and conveying the optional micro-armored cable, 150, for conveying power and data between the behavior director located inside the beak and the storage compartment, 110.

In a reduced size from the one in FIG. 1A and FIG. 1B, the director is applicable to guiding birds in flight over long distances and with precision destinations. As illustrated in FIG. 3, the storage compartment is supported and stabilized to a very difficult to attach to animal. A unique collar and tail-loop assembly provides stability and prevents rotation in the Saggital plane. To protect damage to feathers the tail-loop assembly is a small, flexible loop around the tail section posterior to the wings and anterior to the tail whose position is protected from shifting to the anterior by the shape which may have a slightly smaller diameter on the posterior end than the anterior preventing excessive anterior shift because the body anterior to the tail-loop assembly has a larger diameter. Shifting of the tail loop to the posterior and anterior shifting of the collar are prevented by the connection of the tail loop to the upper portion of the collar, the tail loop to the leggings, and the leggings to the collar. Though this connection may be fabric or net or a combination, its flexibility has a defined limit for stability.

The collar, in the ideal embodiment, has a slightly smaller diameter anterior than posterior which stabilizes and provides protection from shifting of the garment body to the posterior while it prevents lodging of the collar around the throat.

Not visible in FIG. 1 is the back sheath which is simply an essentially non-stretchable fabric and/or net with anterior connections to the collar and posterior connection to the tail loop assembly and lateral connections to the leggings via the garment body. The garment body is a fabric and/or net which connects and stabilizes all the other elements, covers much of the body without preventing ventilation but avoids the wing travel areas, and allows some stretching in the leggings area along the Saggital Plane but none at all along the transverse plane to prevent the load in the storage compartment from shifting to one side or the other and irritating the areas of ascension of the upper wings.

Because of the importance of protecting feathers and not encumbering the wings because of the damage in long flights, the control of load shifting and misalignment of the assembly along the transverse plane (around the roll axis) is largely accomplished by connecting the leggings that are around the upper legs to the collar, tail-loop assembly, and back sheath through the garment body. The legs, because, though they provide much range of flexion and extension along the saggital plane, provide almost no rotation at all along the transverse plane making them the ideal body element for prevention of shifting around the roll axis. For this reason, the fabric and/or netting of the garment body may have flexible fibers allowing stretch along the saggital plane (from front to back) but will have largely inflexible fibers in the body garment running around the body (around the roll axis) which permit almost no stretching that would allow the load to shift laterally around the roll axis.

The combination of the collar, tail loop, body garment, leggings, and back sheath with controlled stretching only in the dimensions ideal for free flight but protection from shifting in any plane, provides a stable but comfortable platform for aligning and carrying equipment of any kind.

In another embodiment primarily adapted for humans, sensors are additionally placed in the transmitter housing, 20 in FIG. 1, or on or around the housing itself. For example, if a person is prone to TMJ, the desired behavior to be directed is associated with a path associated with proper mastication which has a signature when sampled by nearby sound or position or pressure transducers, other sensors or any combinations thereof. These transducers may be placed between the orthosis' anchor wire and the tooth or other preferable position where they can best receive the sounds and/or vibrations and/or position pressures on the elements of the mouth. Improper mastication also has a set of recognizable signatures not associated with tooth contact including the sound of the joint "popping" and the misalignment of the jaw for healthy mastication. The primary source of this sound and vibration, coming from the right and/or left but normally predominant to one side, are indications of improper mastication and also can indicate the direction of correction required which the director can then direct. The contact transducers already mentioned will pick up some of these but specially placed sound transducers will provide improved reception of the sounds and/or vibrations associated with the potential for joint trauma.

An additional orthosis connected to the one shown in FIG. 1A and FIG. 1B located opposite the one so illustrated (if the one in FIGS. 1A and B is an upper mouth orthosis, then this new one would be similarly anchored in the lower mouth) can provide additional pre-contact information. By placing a tiny, flexible bend sensor or other position sensing sensor (which may be similar to the substrate coated bend sensors commonly used in robotics) between the two orthoses, the processor monitoring all these sensors may recognize an inappropriate approach even prior to contact by recognizing a jaw alignment congruent with a bend position associated with joint trauma or poor tooth contact.

So, when, for example, the sensors report an unhealthy signature representative of an improper shift prior to contact from joint position monitoring sensors and/or the recognition of unhealthy signatures at contact as teeth contact at improper points or with improper vectors, as sensed on the contact or other nearby transducers causing a higher or lower pitch on that tooth's sensor and/or a recognizable time period or group signature), the processor will immediately stimulate for a path adjustment in opposition to the harmful path being executed. For example, if the contact points are sensed to have a lateral error (ex: the contact is left of the ideal landing zone). When a problem is sensed prior to contact, the bad contact may be avoided (including the accidental biting of the inner cheek and lips which cause ulceration and possible oral infection). When sensed at or after contact, the wearer is directed towards the preferred placement prior to the next contact. For example, if the contact is striking or will strike too far to the left, the matrix, 10 in FIG. 1A, and/or the ring nodes, 40, may point in the preferred direction, right, with amplitude of stimulation or other recognizable nature of the signal indicating the degree/amount of adjustment needed.

The same sensors in the current invention also easily recognize nocturnal tooth grinding and may be effectively employed to prevent that by a directional stimulation such as a moving arrow to the rear to indicate "stop" all the way up to a strongly interruptive stimulation of all nodes up to a potentially painful degree if previous stimulations have been ignored as monitored by the processor which controls the stimulations and can keep statistics over time to monitor the effectiveness of the previous levels of stimulation and increase as necessary and decrease as appropriate.

External power can be ported to the director in a number of ways. In the ideal configuration, the director chassis contains a battery. For alternative or additional power, a wire can lead from the director to external power from an external source including in the storage compartment. Or, as is becoming more practical, external power can be beamed to it in an induction-based or other wireless energy transfer method.

But that is not what is claimed. Having described the invention, modifications will be evident to those skilled in the art without departing from the scope of the invention as defined in the appended claims.

I claim:

1. A device for the direction of a living body comprising:
a plurality of stimulators whose positions indicate a selected one of the group comprising: A. a spatial direction, B. a pattern relatable to a behavior and C. any combinations of A and B; and
a behavior controller operatively connected to stimulators for directing stimulations; and
a data communication device for communications between the behavior controller and external sources of a selected one of the group comprising: A. data, B. human-directed control, C. computer-directed control, and D. combinations of A, B, and C; and
a power source for the provision of power to components requiring power;
whereby a potentially distant entity can direct the wearer of the device to perform potentially complex actions.

2. The device of claim 1, wherein: the communication device is effected by a selected one of the group comprising A. radio, B. wire, C. video transmission, D. infra-red transmission, F. any practical wireless means of data communication, and F. any combination of A, B, C, D, and F.

3. The device of claim 1, wherein: the stimulators are located in the mouth.

4. The device of claim 1, further comprising: a self-attaching housing for enabling the components to be placed in and removed from the mouth.

5. The device of claim 1, wherein: the location of a stimulation from a stimulator indicates a direction.

6. The device of claim 1, wherein: the location of a stimulation from stimulation means indicates the amount of change desired.

7. The device of claim 1, wherein: the location of a stimulation from stimulation means indicates both a direction and the amount of change desired.

8. The device of claim 1, wherein: a series of points indicated by stimulation means create the perception of a line, or arrow, or shape, or any combination thereof to indicate a direction.

9. The device of claim 1, wherein: a series of points indicated by stimulators creates the perception of a selected one of the group comprising A. line, B. arrow, C. shape, and D any combination of A, B, and C to indicate a distance to be achieved.

10. The device of claim 1, wherein: a series of points indicated by stimulation means create the perception of a line, or arrow, or shape, or any combination thereof to indicate both the direction and the amount of distance to be communicated.

11. The device of claim 1, wherein: a series of points indicated by stimulation means create the perception of a line, or arrow, or shape, or any combination thereof with said points occurring over time to create a perceived motion;
whereby the direction can be emphasized by the moving pattern moving in that direction, or the distance to be communicated can be communicated by the length of the pattern, or the speed desired to be communicated can be communicated by the timing delays between the sequential stimulations, or any combination thereof.

12. The device of claim 1, wherein: a plurality of stimulators are arrayed in a roughly circular or semi-circular area so that they may be related by the mind to direction;
whereby a stimulation at a point in the roughly circular or semi-circular array corresponding to a direction in the current environment may be perceived as an indication of angle or degrees of change.

13. The device of claim 1 further comprising: a sensor operatively connected to the behavior controller for sensing a selected one of the group comprising A. direction, B. attitudes, C. speed, and D. any combination of A, B, and (2; of the body; whereby the behavior controller can monitor and automatically respond to user performance.

14. The device of claim 1 further comprising: a sensor operatively connected to the behavior controller for sensing a selected one of the group comprising A. sounds, B. vibrations, and C. any combination of A and B;
whereby the behavior controller may monitor to sense potential problems or undesirable behavior and stimulate a corrective behavior to correct it.

15. The device of claim 14, wherein: all or part of the assembly is in or adequately proximate to the mouth; whereby TMJ, or tooth grinding, or cheek biting, or snoring or other detrimental oral activities, or any combination thereof, are prevented or minimized by corrective actions directed by the behavior controller.

16. The device of claim 1 further comprising: a battery for provision of power.

17. The device of claim 1, wherein: power, or additional power, or backup power, or any combination thereof for the behavior controller, or any elements of the assembly requiring power, or any combination thereof, are provided by a wire, or any wireless power transmission means, or any combination thereof.

18. The device of claim 1, wherein: behavior controller means includes a fully functional computer processor.

19. The device of claim 1 further comprising: GPS (Global Positioning System) means operatively connected to behavior controller means; whereby behavior controller means can manage the behavior of the body being directed with respect to a map, or a path, or a direction, or an area on the map, or any combination thereof by comparing the actual GPS position with a desired position and directing the body accordingly.

20. The device of claim 1 further comprising: a remote controller located external to the behavior controller for allowing a selected one of the group comprising A. a person, B. a machine, and C. any combination of A and B, to monitor the status of the body and direct its actions by sending instructions to the behavior controller; and a data transmitter operatively connected to the behavior controller and remote controller for allowing communications between them;
whereby the remote controller can manage the behavior of the body being directed.

21. The device of claim 20 further comprising: GPS operatively connected through the data transmitter to the remote controller;

whereby the remote controller can manage the path of the body being directed.

22. The device of claim 20 further comprising: a video camera operatively connected to the remote controller through the data transmitter.

23. The device of claim 20 further comprising: a pointing means operatively connected to remote control means for selecting a desired direction or point;
   whereby any graphical, or GPS map-based, or video-based image, or any combination thereof available to the remote control means can help a remote operator quickly identify a desired point or direction by pointing it out on the image with a mouse, or joystick, or any other point or area identifying device.

24. The device of claim 20 further comprising:
   a steering means;
   whereby a remote operator may steer the remote body with a steering wheel, joystick, keyboard, or any other device capable of left-right steering control and the remote control means can translate those actions to desired directions of change which will result in stimulations directing those changes.

25. The device of claim 24, wherein: the remote operator's directing device additionally provides a third dimension of control;
   whereby the directing device, which may be a joystick or any directing mechanism capable of three-dimensional control, can also direct a third dimension of direction.

26. The device of claim 20 further comprising:
   speed control means;
   whereby the remote operator, using any kind of accelerator, brake, joystick, or any other combination of user-interface control devices, can indicate an increase or decrease in the desired speed which is ultimately converted into stimulations delivered to the body.

27. The device of claim 1, wherein: the stimulators have or include a positive reinforcement component; whereby a selected one of the group comprising A. pleasant vibrations, B. cooling points, C. stimulations that will be perceived as positive to the body, and D. any combination of A, B, and C, are delivered to encourage a positive behavior.

28. The device of claim 27, wherein: positive stimulations are made to erogenous zones.

29. The device of claim 1, further wherein the stimulators provide positive reinforcement for obedience, or negative reinforcement for disobedience or both.

30. The device of claim 29, wherein: other external rewards, or punishments, or teaching aids, or any combination thereof are incorporated by the automated procedure to enhance the speed and depth of the learning experience; whereby visual aids, video images to prompt a behavior, or auditory prompts, or dispensed reward treats, or other useful teaching aids that can be directed by a computer, or any combination thereof, allow more rapid and pleasant automated training.

* * * * *